United States Patent [19]
Ryder

[11] Patent Number: 5,379,760
[45] Date of Patent: Jan. 10, 1995

[54] POSITION INSENSITIVE LOW RESISTANCE ASPIRATOR

[76] Inventor: Steven L. Ryder, 1334 W. Woodcrest Ave., Fullerton, Calif. 92633

[21] Appl. No.: 966,689

[22] Filed: Oct. 26, 1992

[51] Int. Cl.⁶ ............................................. A61M 15/00
[52] U.S. Cl. .......................... 128/200.21; 128/200.18; 128/204.13; 261/78.2; 239/338
[58] Field of Search ...................... 128/200.14, 200.21, 128/200.18, 204.13, 203.12, 204.14; 261/78.2, DIG. 65; 239/342, 338, 346

[56] References Cited
U.S. PATENT DOCUMENTS

| | | | |
|---|---|---|---|
| 1,312,117 | 8/1919 | Hinkle | 128/204.13 |
| 2,311,578 | 2/1943 | Rose | 128/204.13 |
| 3,483,866 | 12/1969 | Macintosh | 128/204.13 X |
| 4,454,877 | 6/1984 | Miller | 128/200.21 |
| 4,652,408 | 3/1987 | Montgomery | 261/130 |

FOREIGN PATENT DOCUMENTS

| | | | |
|---|---|---|---|
| 757158 | 12/1933 | France | 128/204.13 |
| 2832225 | 2/1979 | Germany | 128/204.13 |
| 3311811 | 10/1984 | Germany | 128/204.13 |

*Primary Examiner*—Edgar S. Burr
*Assistant Examiner*—Eric P. Raciti
*Attorney, Agent, or Firm*—Roy A. Ekstrand

[57] ABSTRACT

A position insensitive low resistance aspirator and nebulizer includes a generally disk-shaped hollow housing having an outwardly extending cylindrical input fitting and an outwardly extending oppositely positioned output fitting. A sleeve extends between the input and output fittings and communicates with the disk-like housing interior through a downwardly facing slot. A porous ring is received within the housing interior and defines a capillary between the outer surface thereof and the interior surface of the cavity. A gas pressure vaporizing assembly receives the liquid within the interior cavity through wicking and capillary action. In alternate embodiments, porous members having a dome shape and an annular cylindrical shape are also used.

9 Claims, 2 Drawing Sheets

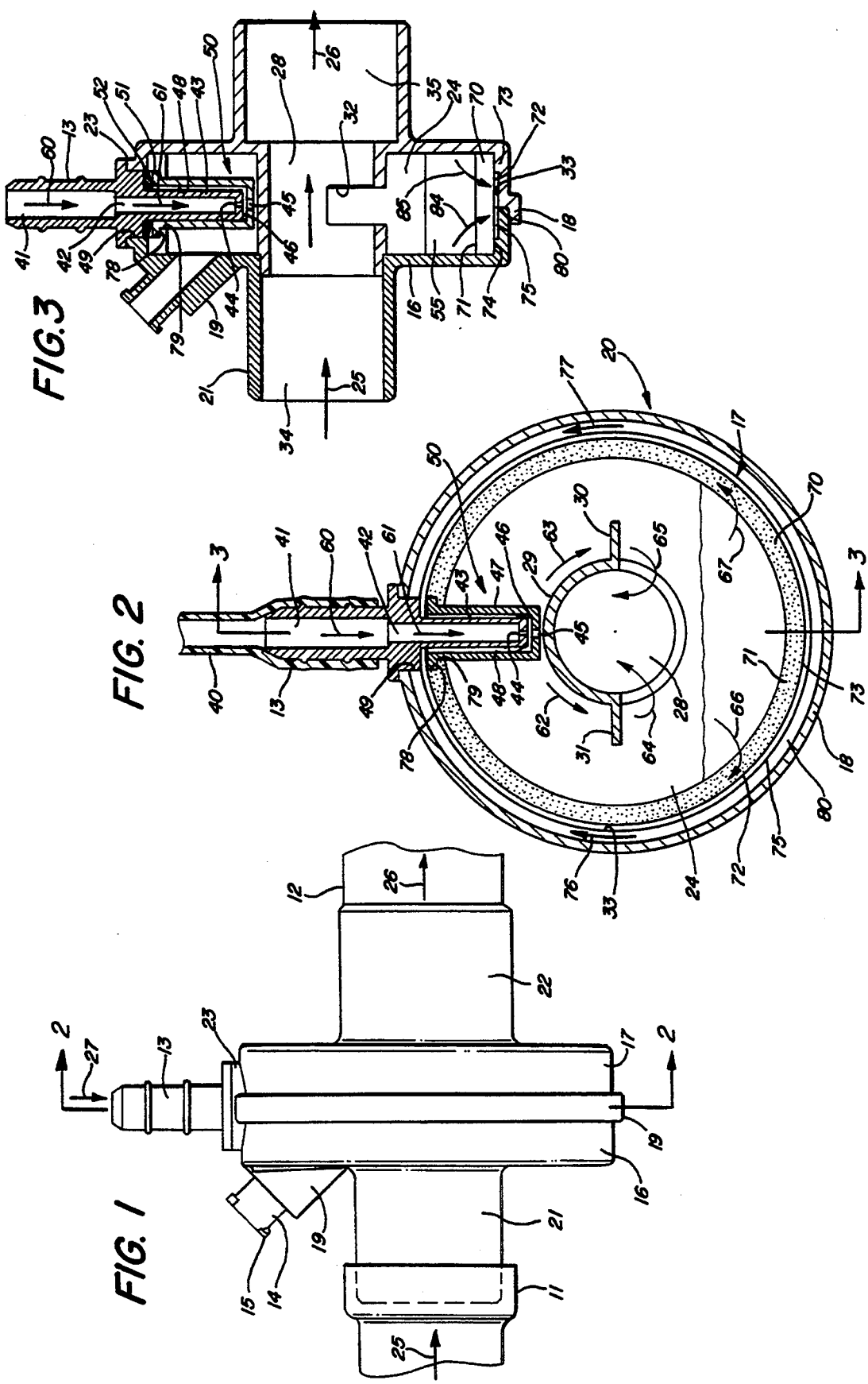

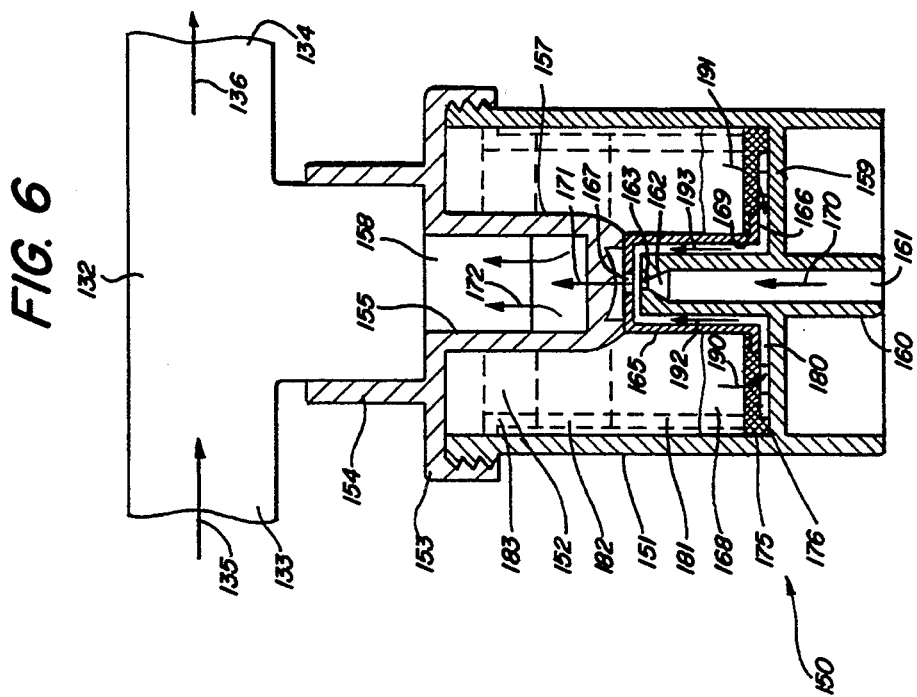
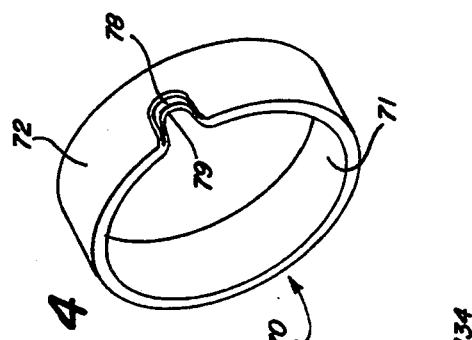
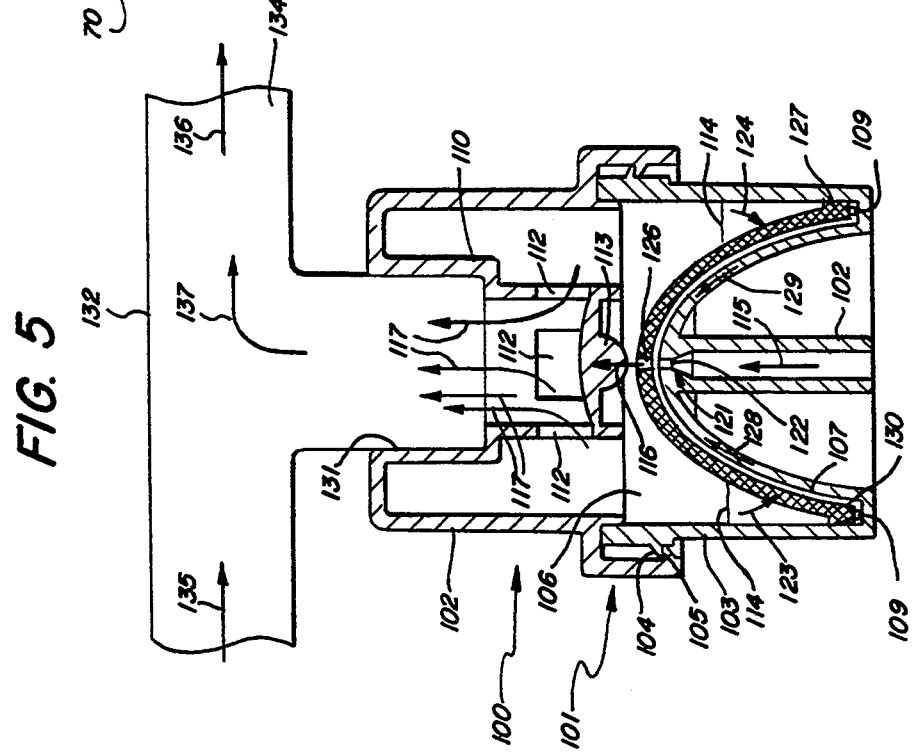

POSITION INSENSITIVE LOW RESISTANCE ASPIRATOR

FIELD OF THE INVENTION

This invention relates generally to apparatus for vaporizing, atomizing or aspirating liquids within a gas and particularly to those used as medical nebulizers.

BACKGROUND OF THE INVENTION

One of the most pervasive extended care patient assisting devices found within most modern hospitals is that known generally as respirators. The general function of such respirators is to aid the breathing function of respiratorily impaired patients while healing and medical treatment proceeds. Such respirators are often utilized in combination with trachea insertion devices as well as oral inhalers. In most respirators, a delivery tube and a return tube couple the respirator to the patient. To aid in treatment and the administering of vaporizable liquid such as medicines or the like, respirators are often provided with a device known generally as a medical nebulizer or simply nebulizer. The basic function of the nebulizer is to vaporize or atomize a liquid and transfer the vaporized or atomized liquid to the airstream on its way to the patient. While a great variety of nebulizer designs have been provided, most generally include a housing having an airflow passage passing therethrough and a reservoir for receiving and holding the to-be-vaporized liquid. A vaporizing chamber is maintained in communication with the airflow passage and means are provided for drawing the liquid into the vaporizing chamber.

Medical nebulizers are subject to several problems some of which are common to nebulizers generally. Perhaps one of the most critical problems or limitations arises in the position sensitivity of most nebulizers. On the one hand, it is desirable in many instances to position the nebulizer relatively close to the patient while on the other hand, the tendency of patients to move about leads to a contrary desire to support the nebulizer some distance from the patient and use an extended delivery tube. When extended delivery tubes are utilized, the possibility of the vaporized liquid condensing within the delivery tube becomes greater which severely limits the effectiveness of the nebulizer and may deprive the patient of the intended dosage of liquid. In addition, the transfer of liquid into the patient's respiratory system is extremely undesirable and may cause harm or discomfort to the patient.

In addition to problems associated with position sensitivity and condensation with the delivery tube, an overall problem or limitation to which nebulizers used in medical apparatus are particularly sensitive is the resistance imposed upon the respiratory airflow by the nebulizer. Many prior art devices provide effective vaporization at the expense of excessive air resistance and have been found on balance to be less than desirable in practical use.

To meet these problems and limitations, practitioners in the art have provided a variety of improved devices both within the medical arts and other related arts. For example, U.S. Pat. No. 5,008,048 issued to Ryder, the applicant of the present application, sets forth a POSITION INSENSITIVE ASPIRATOR which includes a hollow housing communicating with a source of carrier gas and a source of gas under pressure. A nozzle is disposed within the hollow housing through which the pressurized gas is directed to produce a high speed stream of gas. An entrainment member defining an aspiration chamber for the liquid is disposed in the housing with the aspiration chamber immediately adjacent to the nozzle outlet in the housing. A multi-directional liquid flow path is defined by the entrainment member edge portions to provide fluid communication regardless of the orientation of the device.

U.S. Pat. No. 4,743,407 issued to Apel, et al. sets forth a EXTERNALLY PRESSURIZED POROUS CYLINDER FOR MULTIPLE SURFACE AEROSOL GENERATION AND METHOD OF GENERATION in which a nebulizer includes a cylindrical gas permeable active surface. A sleeve is disposed around the cylinder and gas is provided from the sleeve to the interior of the cylinder formed by the active surface. In operation, a liquid is provided to the inside of the gas permeable surface which is wetted with the to-be-vaporized liquid.

U.S. Pat. No. 4,993,436 issued to Bloom, Jr. sets forth an ASPIRATING AND VOLUTIZING LIQUID DISPENSER in which a container and a mouthpiece are adapted to deliver a volutizable liquid orally to the user. A volutizing chamber is defined between the liquid reservoir and the container and the drawing passage in the mouthpiece through which the user inhales. A permeable fluid barrier separates the liquid in the reservoir from the open pore material which fills the volutizing chamber and limits the amount of liquid which can be aspirated through the open pore material to the user.

U.S. Pat. No. 4,512,341 issued to Lester sets forth a NEBULIZER WITH CAPILLARY FEED in which the feed to the spray nozzle is through a narrow space between the flat bottom of the liquid reservoir and a flange fixed to the bottom of the spray nozzle, where the space is narrow enough to draw liquid toward the spray nozzle by capillary action and aspiration at any orientation of the nebulizer between vertical and horizontal.

While the foregoing described devices representative of the prior art have, in some instances, provided improved nebulizer performance and capability, there remains nonetheless a continuing need in the art for ever more improved and effective nebulizing devices.

SUMMARY OF THE INVENTION

Accordingly, it is a general object of the present invention to provide an improved nebulizer. It is a more particular object of the present invention to provide an improved nebulizer which is position insensitive and which offers relatively low resistance to the carrier passing through the nebulizer.

In accordance with the present invention, there is provided for use in vaporizing a liquid and combining the vaporized liquid with a gas flow, a nebulizer comprises: a housing defining an interior cavity for receiving a quantity of to-be-vaporized liquid, an input fitting and an output fitting; an atomizer supported by the housing and extending into the cavity; and a liquid pervious porous member coupled between the atomizer and the quantity of liquid for absorbing the liquid and carrying it to the atomizer.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 sets forth a side elevation view of a nebulizer constructed in accordance with the present invention;

FIG. 2 sets forth a section view of the present invention nebulizer taken along section lines 2—2 in FIG. 1;

FIG. 3 sets forth a section view of the present invention nebulizer taken along section lines 3—3 in FIG. 2;

FIG. 4 sets forth a perspective view of the porous sleeve member utilized in the present invention nebulizer;

FIG. 5 sets forth a section view of an alternate embodiment of the present invention nebulizer; and FIG. 6 sets forth a section view of a further alternate embodiment of the present invention nebulizer.

DESCRIPTION OF THE PREFERRED EMBODIMENTS

FIG. 1 sets forth a side elevation view of a nebulizer constructed in accordance with the present invention and generally referenced by numeral 10. Nebulizer 10 includes a housing 20 comprising a pair of half portions 16 and 17 joined by an annular lip 18 to form a hollow generally cylindrical disk-shaped housing. Housing 20 further includes a generally cylindrical input fitting 21 extending outwardly from half portion 16 and a generally cylindrical output fitting 22 extending outwardly from half portion 17. Housing 20 further defines an upwardly extending cylindrical boss 23 which receives and supports a pressurized gas coupler 13 in the manner set forth below in greater detail. An angularly disposed boss 19 extends outwardly from half portion 16 and supports a cylindrical input tube 14. A cap 15 is removably secured to the outer portion of liquid input tube 14.

In its anticipated operation, pressurized gas coupler 13 is coupled to a source of pressurized gas such as air or oxygen (not shown) while input fitting 21 is coupled to input line 11 which in turn is coupled to the output or delivery tube of a conventional respirator (not shown). Output fitting 22 is coupled to output line 12 which in turn is coupled to the patient's respiratory input such as an inhaler or tracheal unit (not shown). In operation, input line 11 receives a flow of air or other gas in the direction indicated by arrow 25. The gas flowing through line 11 is coupled through fitting 21 to the interior of housing 20 and thereafter outwardly from housing 20 through output fitting 22 and output line 12 in the direction indicated by arrow 26. Concurrently, a supply of to-be-vaporized liquid is deposited within the interior of housing 20 through removal of cap 15 and introduction through liquid input tube 14 and angled boss 19. The flow of pressurized gas into housing 20 from coupler 13 picks up the liquid within housing 20 by means set forth below in great detail and vaporizes the liquid within the interior of housing 20 permitting it to be carried to the patient as the gas flow through housing 20 in the directions indicated by arrows 25 and 26 is carried forward. The operation of vaporizing the liquid within housing 20 and combining it with the gas flowing through housing 20 is carried forward in accordance with an important aspect of present invention which is set forth below in greater detail in conjunction with FIGS. 2 and 3. However, suffice it to note here that the liquid introduced is collected within the lower portion of housing 20 and carried upwardly to pressurized gas coupler 13 by a combination of wicking action as well as capillary action provided by an annular porous member supported within housing 20 and better seen in FIG. 2. Thus, as pressurized gas flows into housing 20 via pressurized gas coupler 13, liquid is vaporized and combined with the primary gas flow in the directions of arrows 25 and 26. As is also set forth below in greater detail, the use of wicking and capillary action to carry liquid within housing 20 to the vaporizing portion of coupler 13 renders nebulizer 10 generally insensitive to position and providing a substantial advantage over most prior art devices. In addition, the straight through primary gas flow between input fitting 21 and output fitting 22 through housing 20 maintains a minimal resistance to the primary gas flow providing yet another advantage of the present invention system. Finally, the position insensitivity or tolerance provided by the present invention nebulizer facilitates the positioning of the present invention nebulizer relatively close to the patient which in turn reduces the length of delivery tube required between the nebulizer and the patient and avoiding the undesired condensation of the vaporized liquid. It should be understood that as used herein the terms such as "vaporized" and "atomized" are generally interchangeable.

While housing 20 may be fabricated using a variety of materials, it has been found advantageous to fabricate half portions 16 and 17 and input fitting 21 and output fitting 22 respectively as integral molded plastic components preferably formed of a clear plastic material. This produces a high strength, lightweight and economical nebulizer unit.

FIG. 2 sets forth a section view of nebulizer 10 taken along section lines 2—2 in FIG. 1. As described above, nebulizer 10 includes a housing 20 formed of half portions 16 and 17 joined by an annular lip 18. In the section view of FIG. 2, half portion 17 is shown and lip 18 is shown in cross section. Housing 20 further defines an interior cavity 24 within which a generally cylindrical sleeve member 29 extends to form a carrier passage 28 through interior cavity 24. Sleeve member 29 further defines a downwardly facing semicircular slot 32 and a pair of outwardly extending generally planar baffles 30 and 31 positioned on either side of the end portions of slot 32. Housing 20 also forms an upwardly extending cylindrical boss 23 having a cylindrical aperture 49 formed therein.

In accordance with an important aspect of the present invention, an annular cylindrical porous ring 70 formed of a liquid pervious porous material is supported within interior cavity 24 of housing 20. Porous ring 70 defines a liquid pervious inner surface 71 and an outer surface 72. As is better seen in FIG. 4, housing 20 further defines a pair of spaced apart annular lip portions 73 and 74 extending inwardly and contacting outer surface 72 of porous ring 70. In further accordance with an important aspect of the present invention, the extension of lip portions 73 and 74 against outer surface 72 produces a thin capillary gap 75 between outer surface 72 of porous ring 70 and inner surface 33 of housing 20. Capillary gap 75 extends between porous ring 70 from either side of aperture 49 of housing 20 and thus generally encircles interior cavity 24. Porous ring 70 further defines a recess 78 and a slot-shaped aperture 79 concentrically arranged with aperture 49 and cylindrical boss 23 of housing 20. A lower nozzle 47 defines a generally cylindrical body received within and extending downwardly through aperture 79 of porous ring 70 and a radially extending lip 51 received within recess 78 thereof. Lower nozzle 47 defines a generally closed end cylindrical member having a nozzle aperture 45 formed at the lower end thereof. Pressurized gas coupling 13 is received within aperture 49 of housing 20 and is seated upon boss 23. Coupling 13 further defines a downwardly extending generally cylindrical upper nozzle 43 having a passage 42 formed therein and a nozzle aperture 44 formed at the lower end thereof. Coupling 13 also defines a passage 41 communicating with passage 42 and aperture 44. In accordance with an important aspect of the present invention, upper nozzle 43 is slightly smaller than lower nozzle 47 and thus is received therein such that a spacing is formed between upper nozzle 43 and lower nozzle 47 which forms a liquid transfer passage 48. Transfer passage 48 is continuous with the upper spacing between lip 51 of lower nozzle 47 and the portion of coupling 13 received within aperture 49. The resulting space between the lower portions of nozzles 43 and 47 forms a film area 46 in communication with transfer passage 48. It should be noted that the upper spacing between coupling 13 and lip 51 of nozzle 47 is generally aligned with capillary gap 75 and thus provides communication between capillary gap 75 and transfer passage 48 as well as film area 46.

In operation with pressurized gas coupling 13 coupled to a source of pressurized gas via a gas supply tube 40 and a quantity of liquid 55 received within interior cavity 24 through input tube 14 (seen in FIG. 1), nebulizer 10 is operative to fill interior cavity 24 with a quantity of vaporized liquid which may then be drawn through carrier passage 28 to be respirated by the patient. More specifically, the porosity of porous ring 70 causes a portion of liquid 55 to be drawn into porous ring 70 in the directions indicated by arrows 66 and 67. The wicking property of porous ring 70 causes this liquid to move upwardly on each side of porous ring 70. In addition, as liquid permeates the entire porous structure of ring 70 and is introduced into capillary gap 75, the liquid rises upwardly within gap 75 due in part to capillary action in the directions indicated by arrows 76 and 77.

Concurrently, the flow of pressurized gas through passages 41 and 42 of coupling 13 in the directions indicated by arrows 60 and 61 forms an increased velocity flow through apertures 44 and 45 due to the Bernouli principle. The high velocity flow through apertures 44 and 45 produces a partial vacuum within film area 46 and transfer passage 48. The effect of this partial vacuum further draws the liquid within capillary gap 75 upwardly in the directions indicated by arrows 76 and 77 producing a liquid flow which ultimately fills transfer passage 48 and produces a liquid film within film area 46. The high velocity gas movement through apertures 44 and 45 in the presence of liquid within film area 46 produces a liquid vaporization which flows outwardly against sleeve 29 in the directions indicated by arrows 62 and 63. Baffles 30 and 31 further deflect this flow of vaporized liquid and gas to the outer portions of interior cavity 24. As respiratory gas flow moves through carrier passage 28 of nebulizer 10, the vaporized liquid is drawn inwardly to carrier passage 28 through slot 32 in the directions indicated by arrows 64 and 65. Thereafter, the vaporized liquid combines with the primary respiratory gas flow and is carried to the patient.

It will be apparent to those skilled in the art that the use of capillary action within capillary gap 75, wicking action of porous ring 70 and the drawing action provided by pressurized gas flow within atomizer 50 combine to assure a reliable flow of liquid to film area 46 for vaporization which is generally independent of the position of nebulizer 10. As will be apparent to those skilled in the art, the porous nature of ring 70 extending generally the entire perimeter of interior cavity 24 assures a transfer of liquid from interior cavity 24 to capillary gap 75 regardless of the position of nebulizer 10. In addition, the relative positions of sleeve 29, baffles 30 and 31 and slot 32 with respect to apertures 44 and 45 of atomizer 50 prevent the direct transfer of vaporized liquid into carrier passage 28 resulting in a more full vaporization and more uniform vapor content in the respiratory gas supplied to the patient.

FIG. 3 sets forth a section view of nebulizer 10 taken along section lines 3—3 in FIG. 2. As described above, nebulizer 10 includes a housing 20 formed of half portions 16 and 17. Half portions 16 and 17 are joined to form a sealed seam 80 and are mutually secured by a lip 18. Thus, housing 20 defines an interior cavity comprising a liquid tight sealed cavity. Half portion 16 further defines a generally cylindrical input fitting 21 having a passage 34 extending therethrough while half portion 17 defines a generally cylindrical output fitting 22 extending outwardly therefrom and defining a passage 35. Half portion 17 further defines a generally cylindrical sleeve 29 having a gas carrier passage 28 and a downwardly facing slot 32 formed therein. In the preferred fabrication of the present invention nebulizer, sleeve portion 29 extends through interior cavity 24 and couples passages 34 and 35 through gas carrier passage 28. Thus, slot 32 forms the sole communication between gas carrier passage 28 and interior cavity 24.

In accordance with an important aspect of the present invention described above, nebulizer 10 further includes an annular porous ring 70 defining a liquid pervious inner surface 71 and a liquid pervious outer surface 72. Housing 20 further defines a pair of inwardly extending annular lip portions 73 and 74 spaced on either side of surface 33 thereby forming a capillary gap 75 between outer surface 72 of porous ring 70 and inner surface 33 of housing 20. Porous ring 70 further defines a slot-shaped recess 78 and an aperture 79. A lower nozzle 47 forms a generally cylindrical member having a radially extending lip 51 and a cylindrical body extending downwardly into interior cavity 24 and defining a nozzle aperture 45 at the lower end thereof. Housing 20 defines a cylindrical boss 23 having an aperture 49 formed therein. Aperture 49 is generally concentric with recess 78 and aperture 79. Accordingly, coupler 13 includes a downwardly extending generally cylindrical upper nozzle 43 having a nozzle aperture 44 at the lower end thereof. Coupler 13 is received within aperture 49 such that upper nozzle 43 extends downwardly into the interior of lower nozzle 47. A gap 52 is formed between coupler 13 and lower nozzle 47 which, as described above, is generally aligned with capillary gap 75. In addition, the smaller size of upper nozzle 43 provides a transfer passage 48 between the outer surface of upper nozzle 43 and the inner surface of lower nozzle 47 as well as a film area 46 between the lower portions of nozzles 43 and 47.

In operation and as described above, a quantity of to-be-vaporized liquid is introduced to interior cavity 24 through liquid input tube 14 and collects in the lower portion of cavity 24 forming a liquid reservoir supply 55. The respiratory gas flow passes through housing 20 via passages 34 and 35 of fittings 21 and 22 respectively as well as carrier passage 28 of sleeve portion 29 in the directions indicated by arrows 25 and 26. Concurrently, a supply of pressurized gas is applied to coupler 13 producing a pressurized gas flow through passages 41 and 42 in the directions indicated by arrows 60 and 61 respectively. The airflow through passage 42 is forced through apertures 44 and 45 of nozzles 43 and 47 respectively increasing the flow velocity as a result and producing a partial vacuum within film area 45 and transfer passage 48 which is communicated to gap 52 and capillary gap 75.

Concurrently, the absorption of liquid 55 into porous ring 70 due to the porous structure thereof and the liquid pervious character of inner surface 71 and outer surface 72 produces a capillary liquid flow within capillary gap 75. This flow is enhanced by the partial vacuum formed in gap 52 causing the to-be-vaporized liquid to be drawn into transfer passage 48 and film area 46. Within film area 46, the liquid is vaporized and carried outwardly through aperture 45. As respiratory gas flows through carrier passage 28 of sleeve 29, this vaporized liquid is drawn into passage 28 through slot 32 and thereafter carried outwardly from housing 20 through passage 35 and on to the patient.

As described above, the use of porous ring 70 and the capillary and wicking action to transfer the to-be-vaporized liquid to atomizer 50 formed by nozzles 43 and 47 provides a position insensitive atomizing process. In addition, the use of sleeve 29 and baffles 30 and 31 further enhances this position insensitivity.

FIG. 4 sets forth a perspective view of porous ring 70 constructed in accordance with the present invention. As described above, porous ring 70 is formed of a liquid porous material and defines a liquid pervious inner surface 71 and a liquid pervious outer surface 72. A recess 78 and a slot-shaped aperture 79 are formed concentrically in porous ring 70. Porous ring 70 may be fabricated using virtually any liquid pervious and porous material. However, it has been found advantageous to fabricate porous ring 70 using a lightweight open celled plastic or similar material.

FIG. 5 sets forth a section view of an alternate embodiment of the present invention which utilizes the novel principle of operation set forth above and which is generally referenced by numeral 100. Nebulizer 100 includes a housing 101 formed of a cylindrical upper portion 102 and a cylindrical lower portion 103. Upper portion 102 defines an inwardly extending lip 105 while lower portion 103 defines an outwardly extending lip 104. Lips 104 and 105 cooperate to secure upper and lower portions 102 and 103 to form housing 101. Upper portion 102 of housing 101 further defines an inwardly extending cylindrical center baffle member 110. Baffle member 110 further defines a cylindrical recess 131 which receives a portion of a conventional T-fitting 132. Center baffle 110 further defines a lower baffle 113 and a plurality of window apertures 112. Lower portion 103 of housing 101 further defines an upwardly extending dome-shaped member 107 which supports a cylindrical coupler 120. Coupler 120 defines a passage 108 terminating in a nozzle portion 121. Nozzle portion 121 includes a tapered portion terminating in a reduced diameter nozzle passage 122.

A porous member 125 shaped in general conformity to center dome 107 is received within the interior of lower portion 103 and supported upon center dome 107 and spaced therefrom by a plurality of spacers 109. Porous member 125 is preferably formed of an open celled lightweight material such as molded plastic or the like and defines a center aperture 126 generally aligned with nozzle passage 122. Porous member 125 further defines an outwardly extending sealing lip 127 which is received against the inner surface of lower portion 103 of housing 101. The combined structures of upper portion 102 and lower portion 103 define an interior cavity 106 within which a quantity of to-be-atomized liquid 114 is received and supported.

T-shaped fitting 132 is of conventional construction and includes an input coupling 133 and output coupling 134 and a center portion which is received within recess 131 of housing 101.

In operation, a source of pressurized gas such as oxygen or air is applied to coupler 120 producing a gas flow therethrough in the direction indicated by arrow 115. A quantity of liquid 114 is absorbed into porous member 125 in the directions indicated by arrows 123 and 124. This liquid is carried upwardly within porous member 125 and a portion thereof is carried into capillary gap 130. A flow of aspirating air or oxygen is carried through T-fitting 132 in the directions indicated by arrows 135 and 136. This airflow tends to draw the gases within nebulizer 100 upwardly and into T-fitting 132 in the direction indicated by arrow 137. Thereafter, these gases are carried through output 134. The flow of gas through coupler 120 is increased in velocity through nozzle 122 and results in the creation of a high velocity gas stream through nozzle passage 122 and aperture 126 of porous member 125 upwardly in the direction indicated by arrow 116. The combined actions of capillary action within gap 130 and the wicking action of porous member 125 provide a supply of liquid in the region of aperture 126 which is atomized by the gas flow through nozzle 121 and carried outwardly as a flow of atomized liquid. Baffle 113 and windows 112 cooperate to diffuse the flow of atomized liquid permitting it to move slowly up through center baffle 110 in the directions indicated by arrows 117. Thereafter, the above-described drawing effect of the gases moving through T-fitting 132 draw the atomized liquid into the primary respiratory flow in the direction indicated by arrow 137.

FIG. 6 sets forth a section view of a still further alternate embodiment of the present invention nebulizer generally referenced by numeral 150. Nebulizer 150 includes a generally cylindrical housing 151 having a threaded cap 153 secured thereto. Housing 151 defines an interior cavity 152 and a generally cylindrical coupler housing 160. Coupler housing 160 is supported by bottom portion 159 of housing 151. Coupler 160 further defines an interior passage 161 terminating in a tapered nozzle portion 162 and an aperture 163. Nebulizer 150 further includes a generally annular porous member 175 having a downwardly extending spacer lip 176 resting upon bottom 159. Porous member 175 defines an aperture 169 which receives and supports a generally cylindrical nozzle sleeve 165. Nozzle sleeve 165 encloses the upper portion of coupler 160 and defines an aperture 167 generally aligned with aperture 163 and nozzle 162.

Cap 153 defines a cylindrical fitting 154 having a passage 158 therethrough. Cap 153 further defines a downwardly extending generally cylindrical center baffle 155 defining a plurality of apertures 172 and a lower baffle 157. A conventional T-fitting 132 includes a center portion received within fitting 154 of cap 153 together with an input coupling 133 and an output coupler 134. T-fitting 132 forms a portion of the respiratory flow to the patient in the directions indicated by arrows 135 and 136.

In accordance with the present invention, a quantity of liquid 168 is received within interior cavity 152 and permeates porous member 175 in the directions indicated by arrows 190 and 191. In further accordance with the present invention, porous member 175 and nozzle sleeve 165 are spaced from bottom 59 and coupler 160 respectively to form a continuous capillary gap 180 therebetween.

In operation, as pressurized gas such as oxygen or air is forced into passage 161 of coupler 160 in the direction of arrow 70, the flow velocity thereof is increased through nozzle 162 and aperture 163 to produce a high velocity flow against baffle 157. Concurrently, liquid 168 is absorbed into porous member 175 and is transferred into capillary gap 180 and carried upwardly in the directions indicated by arrows 192 and 193 to the region of aperture 163. The high velocity flow then carries the liquid outwardly through aperture 167 in the form of atomized liquid which is diffused by baffle 157 and drawn upwardly through apertures 156 in the directions indicated by arrows 172. Thereafter, the drawing action of respiratory airflow through fitting 132 draws the atomized liquid into the main flow in the manner indicated by arrow 137 carrying it to the patient. It should be noted that while FIG. 6 sets forth a porous member 175 having a generally annular shape, the embodiment of FIG. 6 may be further modified in accordance with user preference to include porous upwardly extending sidewalls shown in dashed line representations 181, 182 and 183 without departing from the spirit and scope of the present invention.

Thus, what has been shown is a position insensitive low resistance aspirator having a relatively simple low cost and easy to manufacture structure. The structure provided utilizes a sealed housing defining an interior cavity having a low resistance respiratory gas flow passage therethrough. Liquid is received with the interior cavity and carried to a gas pressure atomizing assembly through a combination of wicking and capillary action which is enhanced by the drawing action of the pressurized gas flow. The resulting structure offers virtually no resistance to respiratory air and is sufficiently positioned insensitive to be used in close proximity to the patient thereby permitting the virtual elimination of the delivery tube portion between the nebulizer and the patient and avoiding undesired condensation of the vaporized liquid.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in vaporizing or atomizing a liquid to form a mist to be combined with a primary gas flow, a nebulizer comprising:

a housing defining an interior cavity for receiving a quantity of to-be-atomized liquid, an interior surface exposed to said interior cavity and an output fitting in communication with said primary gas flow;

an atomizer supported by said housing and extending into the cavity having an upper nozzle and a lower nozzle, said nozzles having respectively first and second nozzle apertures, said apertures being separated by a film passage, and said film passage being in communication with a liquid transfer passage;

a secondary gas inlet in communication with said atomizer for forming a secondary gas flow;

a liquid pervious porous member supported within said interior cavity overlying said interior surface spaced therefrom to form a liquid transfer gap therebetween; said liquid transfer gap and said liquid pervious porous member being in communication with said liquid transfer passage;

wherein said liquid-to-be-atomized is moved through said liquid pervious porous member by capillary action and wherein said secondary gas flow passes through said atomizer a negative pressure is induced in said liquid transfer passage for aspirating liquid from said liquid pervious porous member and said liquid transfer gap and subsequently into said film passage for atomization.

2. A nebulizer as set forth in claim 1 wherein said liquid pervious porous member is formed of an open cell material.

3. A nebulizer as set forth in claim 1 wherein said interior surface and said liquid pervious porous member are generally annular.

4. A nebulizer as set forth in claim 1 wherein said interior surface and said liquid pervious porous member are generally convexly dome-shaped.

5. A nebulizer as set forth in claim 1 wherein said interior surface and said liquid pervious porous member are generally cylindrical.

6. A nebulizer as set forth in claim 1 wherein said interior surface and said liquid pervious porous member are generally convexly curved.

7. A nebulizer as set forth in claim 1 further including an input port formed in said housing communicating with said interior cavity thereof for adding liquid to said interior cavity.

8. A nebulizer as set forth in claim 1 wherein said housing is generally cylindrical and wherein said liquid pervious porous member is generally cylindrical and received within said housing.

9. A nebulizer as set forth in claim 8 wherein said housing defines an annular recess and wherein said liquid pervious porous member is supported upon said interior surface forming a capillary gap therebetween.

* * * * *